(12) United States Patent
Takahashi et al.

(10) Patent No.: US 6,506,370 B1
(45) Date of Patent: *Jan. 14, 2003

(54) HAIR-GROWING AGENT

(75) Inventors: Tomoya Takahashi, Tsushiura (JP);
Yoshiharu Yokoo, Ushiku (JP);
Toshikazu Kamiya, Machida (JP);
Akio Shirai, Machida (JP); Tatsuya Tamaoki, Machida (JP)

(73) Assignee: Kyowa Hakko Kogyo Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/826,072

(22) Filed: Mar. 24, 1997

(30) Foreign Application Priority Data

Mar. 29, 1996 (JP) .............................. 8-075903

(51) Int. Cl.⁷ .................. A61K 7/06; A61K 31/185
(52) U.S. Cl. .................. 424/70.1; 424/70.11; 530/319; 514/2; 514/75; 514/131; 514/139; 514/557; 514/558; 514/765

(58) Field of Search .............................. 530/319; 514/2, 514/557, 558, 75, 131, 765, 139; 424/70.1, 70.11

(56) References Cited

U.S. PATENT DOCUMENTS

| | | | | |
|---|---|---|---|---|
| 4,723,950 A | * | 2/1988 | Lee ............................. 604/322 |
| 5,013,545 A | * | 5/1991 | Blackman et al. ............. 424/81 |
| 5,049,552 A | * | 9/1991 | Eibl ............................. 514/77 |
| 5,407,670 A | * | 4/1995 | Shinault .................. 424/78.06 |
| 5,800,385 A | * | 9/1998 | Demopulos et al. ..... 604/890.1 |

OTHER PUBLICATIONS

C.S. Harmon: "Bisindolylmaleimide protein kinase C inhibitors are potent stimulators of DNA synthesis in mouse hair follicle organ cultures"; J. Invest. Dermatol., vol. 104, No. 4, 1995 p. 606, XP002035589 *abstract*.

Databse WPI, Section Ch, Week 9223, Derwent Publications Ltd., London, GB, AN 92–189207, XP002035591 & JP 04 124 122 A (Shiseido Co Ltd), Apr. 24, 1992 *abstract*.

* cited by examiner

*Primary Examiner*—Christopher S. F. Low
*Assistant Examiner*—Anish Gupta
(74) *Attorney, Agent, or Firm*—Antonelli, Terry, Stout & Kraus, LLP

(57) ABSTRACT

Disclosed is a safe and effective hair-growing agent comprising a protein kinase C-specific inhibitor.

8 Claims, No Drawings

HAIR-GROWING AGENT

FIELD OF THE INVENTION

The present invention relates to a hair-growing agent comprising a protein kinase C-specific inhibitor.

BACKGROUND OF THE INVENTION

There is disclosed that substances with a protein kinase-inhibiting activity, 3-amino/hydroxy-4-[4-benzoyl-phenyl carbonylamino/oxy]azepanes stimulate the growth of hair (EP663393 A1); but said proteinkinase inhibitors have a protein kinase A (hereinafter referred to as PKA)-inhibiting activity along with a protein kinase C (hereinafter referred to as PKC)-inhibiting activity.

In hair-follicle organ culture systems, a PKC inhibitor, H-7 is known to release the hair growth-retarding activity of a PKC-activating substance, 12-O-tetragalloyl-phorbol-13-acetate (British Journal of Dermatology, 133, 5, 686–693, 1995). Said H-7 is further known to have a PKA-inhibiting activity along with a PKC-inhibiting activity (BIO/TECHNOLOGY, 8, 732, 1990).

In hair-follicle organ culture systems, the PKC inhibitor, H-7 releases the hair growth-inhibiting activity of 12-O-tetragalloyl-phorbol-13-acetate, but said PKC inhibitor has not been known to have a hair growth-promoting activity (British Journal of Dermatology, 133, 5, 686–693, 1995).

Protein kinase inhibitors having both a PKC-7inhibiting activity and a PKA-inhibiting activity could not always be expected to produce satisfactory hair growth-promoting results. H-7 and 3-amino/hydroxy-4-[4-benzoyl-phenyl carbonylamino/oxy]azepanes could not always be expected to produce satisfactory hair growth-promoting results, because such compounds have both a PKC-inhibiting activity and a PKA-inhibiting activity.

The present inventors have first found that PKC-specific inhibitors produce satisfactory hair growth-promoting results.

SUMMARY OF THE INVENTION

The object of the present invention is to provide a safe and effective ahir-growing agent comprising, as an active ingredient, a PKC-specific inhibitor, and pharmaceutically acceptable vehicles.

DETAILED DESCRIPTION OF THE PRESENT INVENTION

The protein kinase C-specific inhibitor as referred to herein is a protein kinase inhibitor having a PKC-inhibiting activity while having a PKA-inhibiting activity as little as possible. Specifically, any inhibitor can be used so long as the ratio of its 50% PKA-inhibiting constant (hereinafter referred to as PKA-$IC_{50}$) to its 50% PKC-inhibiting constant (hereinafter referred to as PKC-$IC_{50}$), PKA-$IC_{50}$/PKC-$IC_{50}$, is not smaller than 3.0 when determining PKC-$IC_{50}$ and PKA-$IC_{50}$ according to the following PKC-inhibiting, activity measuring method and according to the following PKA-inhibiting activity measuring method, respectively. For example, usable herein are protein kinase inhibitors having PKA-$IC_{50}$/PKC-$IC_{50}$/PKC-$IC_{50}$ of from 10 to $10^9$.

For determination of PKA-inhibiting activity of protein kinase inhibitors having a low PKA-inhibiting activity, the following method requires a large amount of such a protein kinase inhibitor to be determined therein, in which, therefore, the protein kinase-inhibiting activities of the protein kinase inhibitor could be measured only up to its uppermost soluble concentration in the system. Accordingly, if such a protein kinase inhibitor with low PKA-inhibiting activity is used, the value of PKA-$IC_{50}$/PKC-$IC_{50}$ capable of being numerically determined in said method will be about up to $10^9$. The protein kinase inhibitors usable: in the present invention have its value of PKA-$IC_{50}$/PKC-$IC_{50}$ of not smaller than 3, without being defined by its upper value of PKA-$IC_{50}$/PKC-$IC_{50}$($10^9$) capable of numerically determined by said method.

Preferred protein kinase inhibitors for use are those having a value of PKA-$IC_{50}$/PKC-$IC_{50}$ of from 10 to $10^9$.

(1) Method for Measuring PKC-inhibiting Activity:

To measure the PKC-inhibiting activity of a protein kinase inhibitor, referred to is the Kikkawa et al's method (Journal of Biological Chemistry, 257, 13341, 1982).

Precisely, 10 $\mu$l of a sample to be tested for determining its activity is added to 250 $\mu$l of a solution comprising 2.5 $\mu$mols of magnesium acetate, 50 $\mu$g of histone Type IIIS (produced by Sigma Co.), 20 $\mu$g of phosphatidylserine, 0.8 $\mu$g of diolein, 25 nmols of calcium chloride, 5 $\mu$g of a crude enzyme (as partially purified from a rat brain according to the Kikkawa et al's method) and 5 $\mu$mols of Tris-HCl buffer (pH 7.5), and incubated therein at 30° C. for 3 minutes.

After the completion of the incubation, 1.25 nmols of [g-$^{32}$P]ATP (from $5\times10^3$ to $10\times10^3$ cpm/nmol) is added to the system, and phosphorylation reaction is carried out at 30° C. for 3 minutes, and thereafter the reaction is terminated by adding 25% trichloroacetic acid thereto.

The resulting reaction mixture is filtrated through a cellulose acetate membrane (pore size: 0.45 $\mu$m) (produced by Toyo Filter Co.), and the membrane is washed four times with 5% trichloroacetic acid, and thereafter the radioactivity of the residue remained on the membrane is measured to be a value of the sample.

On the other hand, the same process as described above is repeated without adding the sample to the system, and the radioactivity is obtained to be a control value.

The molar concentration of the sample having the value of radioactivity which is 50% of the control value is obtained to be the 50% PKC-inhibiting constant (PKC-$IC_{50}$) of the sample.

(2) Method for Measuring PKA-inhibiting Activity:

To measure the PKA-inhibiting activity of a protein kinase inhibitor, referred to is the Kuo et al's method (see Biochemistry, 6, 1349, 1969).

Precisely, 10 $\mu$l of a sample to be tested for determining its activity is added to 250 $\mu$l of a solution comprising 5 $\mu$mols of Tris-HCl buffer. (pH 6.8), 2.5 $\mu$mols of magnesium acetate, 100 $\mu$g of histone Type IIS (produced by Sigma Co.), 0.25 nmols of c-AMP and 200 $\mu$g of a crude enzyme (as partially purified from a calf heart according to the Kuo et al's method), and incubated therein at 30° C. for 3 minutes.

After the completion of the incubation, 1.25 nmols of [g-$^{32}$P]ATP (from $5\times10^3$ to $10\times10^3$ cpm/nmol) is added to the system, and phosphorylation reaction is carried out at 30° C. for 3 minutes, and thereafter the reaction is terminated by adding 25% trichloroacetic acid thereto.

The resulting reaction mixture is filtrated through a cellulose acetate membrane (pore size: 0.45 $\mu$m) (produced by Toyo Filter Co.), and the membrane is washed four times with 5% trichloroacetic acid, and thereafter the radioactivity of the residue remained on the membrane is measured to be a value of the sample.

On the other hand, the same process as described above is repeated without adding the sample to the system, and the radioactivity is obtained to be a control value.

The molar concentration of the sample having the value of radioactivity which is 50% of the control value is obtained to be the 50% PKA-inhibiting constant (PKA-IC$_{50}$) of the sample.

Specific examples of the protein kinase C-specific inhibitor for use in the invention may include polymyxin B, calphostin C, palmitoyl-DL-carnitine and hexadecylphosphocholine (militefosine, produced by Sigma Co.), and also their pharmaceutically-acceptable salts.

The pharmaceutically-acceptable salts may include, for example, hydrochlorides, hydrobromides, sulfates, nitrates, formates, acetates, benzoates, maleates, fumarates, succinates, tartrates, citrates, oxalates, methanesulfonates, toluenesulfonates, aspartates, and glutamates.

The hair-growing agent of the present invention may be taken any form, provided that it properly contains the protein kinase C-specific inhibitor of the invention. For example, a liquid or solid hair-growing agent comprising the protein kinase C-specific inhibitor of the invention along with pharmaceutically acceptable vehicles is used.

The liquid or solid hair-growing agent may include liquid-type preparations such as hair liquids, hair tonics and hair lotions; and solid-type preparations such as ointments and hair creams. These agents can be prepared by any ordinary methods, while adding the protein kinase inhibitor of the invention to suitable vehicles.

The amount of the protein kinase C-specific inhibitor to be in the hair-growing agent of the present invention greatly varies, depending on the intensity of its inhibiting activity and also on its endermic absorbability to be derived from its physical properties, but may be generally from $10^{-6}$ to 10% by weight (hereinafter referred to as %) based on the agent in terms of the content of a single compound of the inhibitor or a mixture of plural compounds thereof.

The preferred vehicles for the liquid-type preparations are those that are generally used in ordinary hair-growing agents, such as pure water, ethanol, polyalcohols, oils and fats. If desired, any additives may be added thereto.

The polyalcohols may include, for example, glycerol, 1,3-butylene glycol, propylene glycol, etc.

The oils and fats may include, for example, wheat germ oil, camellia oil, Jojoba oil, olive oil, squalane, safflower oil, macadamia, nut oil, avocado oil, hydrogenated soybean lecithin, etc.

The additives may include, for example, fragrances, surfactants, microbicides, etc. If desired, any of antioxidants, hormones, ultraviolet absorbents, anti-inflammatory agents, refrigerants, moisturizers, vitamins, herb extracts, tinctures, etc. may be added to the preparations.

As the fragrances, any fragrance usable in ordinary cosmetics, etc. are employable herein.

The surfactants may include, for example, polyoxyethylene(60) hardened castor oil, polyoxyethylene(8) oleyl ether, polyoxyethylene(10) oleyl ether, polyoxyethylene(10) monooleate, polyoxyethylene(30) glyceryl monostearate, sorbitan monostearate, polyoxyethylene(30) glyceryl monostearate, polyoxyethylene(20) sorbitan monooleate, sucrose fatty acid esters, hexaglycerin monooleate, hexaglycerin monolaurate, polyoxyethylene reduced lanolin, polyoxyethylene(20) lanolin alcohol, polyoxyethylene(25) glyceryl pyroglutamate isostearate diester, N acetylglutamine isostearyl ester, etc.

The microbicides may include, for example; trichlorohydroxydiphenyl ether, hinokitiol, tricrosan, chlorohexidine gluconate, phenoxyethanol, resorcinol, isopropylmethylphenol, azulene, salicylic acid, zinc pyrithione, benzalkonium chloride, photoreceptor No. 301, sodium mononitroguaiacol, etc.

The antioxidants may include, for example, butylhydroxyanisole, propyl gallate, and erysorbic acid.

The hormones may include, for example, ethynylestradiol, estrone, estradiol, etc.

The ultraviolet absorbents may include, for example, benzophenones such as dihydroxybenzophenone; as well as melanins, ethyl para-aminobenzoate, 2-ethylhexyl paradimethylaminobenzoate, cinoxate, 2-ethylhexyl paramethoxycinnamate, 2-(2-hydroxy-5-methylphenyl)benzotriazole, urocanic acid, and fine particles of metal oxides, etc.

The anti-inflammatory agents may include, for example, dipotassium glycyrrhetinatel β-glycyrrhetinic acid, allantoin, diphenhydramine hydrochloride, guaiazulehe, and 1-menthol, etc.

The refrigerants may include, for example, capsicum tincture, 1-menthol, etc.

The moisturizers may include, for example, L-pyrrolidonecarboxylic acid, sodium hyaluronate, chondroitin sulfate, etc.

The vitamins may include, for example, dl-α-tocopherol acetate, dl-α-tocopherol, d-δ-tocopherol, vitamin E, benzyl nicotinate, nicotinic acid amide, D-pantothenyl alcohol, pantothenylethyl ether, biotin, pyridoxine hydrochloride, riboflavin, etc.

The herb extracts may include, for example, Swertia herb extract, garlic extract, ginseng extract, aloe extract, cinchona extract, etc.

The tinctures may include, for example, capsicum tincture, ginger extract, cantharis tincture, etc.

Where the above-mentioned liquid-type preparations are used as spray, they may be combined with noninflammable gas or the like.

The vehicles for the solid-type preparations may include, for example, vaseline, solid paraffin, vegetable oil, mineral oil, lanolin, wax, and macrogol. To these may be added, if desired, any of the above-mentioned additives; emulsifiers such as lecithin; and lower alcohols such as ethyl alcohol, isopropyl alcohol, etc.

The amount of the hair-growing agent of the present invention to be applied varies, depending on the age, the body weight and the condition of the case to which it is applied, the curing effect of said agent, the mode of administration, the treating time, etc. For a hair tonic of the hair-growing agent of the present invention, for example, its percutaneous dose may be from 0.5 to 5 ml/adult, preferably from 1 to 3 ml/adult, and may be applied once or several times a day.

Now, the present invention is described in more detail hereinunder with reference to the following examples, reference example and test examples.

EXAMPLE 1

Preparation of Hair-growing Agent Tonic 1

First, 55 g of ethyl alcohol, 7 g of 1,3-butyleneglycol, 0.5 g of N-acetylglutamine isostearyl ester, and 0.25 g of polyoxyethylene(25) glyceryl pyroglutamate isostearate diester were uniformly mixed and stirred to prepare a solution A.

Next, 0.3 g of polymyxin B sulfate (produced by Sigma Co.) and 36.95 g of pure water was uniformly mixed and stirred to prepare a solution B.

The solution B was added to the solution A with stirring, and uniformly mixed to prepare a hair-growing agent tonic (composition 1).

EXAMPLE 2

Preparation of Hair-growing Agent Tonic 2

First, 90 g of ethyl alcohol, 5 g of 1,3-butyleneglycol, 0.5 g of N-acetylglutamine isostearyl ester, 0.25 g of polyoxyethylene(25) glyceryl pyroglutamate isostearate diester, and 0.03 g of calphostin C (produced by Kyowa Hakko Kogyo Co., Ltd) were uniformly mixed and stirred to prepare a solution A.

To the solution A was added 4.22 g of pure water with stirring, and uniformly mixed to prepare a hair-growing agent tonic (composition 2).

EXAMPLE 3

Preparation of Hair-growing Agent Tonic 3

First, 77 g of ethyl alcohol, 10 g of 1,3-butyleneglycol, 0.5 g of N-acetylglutamine isbstearyl ester, 0.25 g of polyoxyethylene(25) glyceryl pyroglutamate isostearate diester, and 3 g of palmitoyl-DL-carnitine hydrochloride (produced by Sigma Co.) were uniformly mixed and stirred to prepare a solution A.

To the solution A was added 9.25 g of pure water with stirring, and uniformly mixed to prepare a hair-growing agent tonic (composition 3).

EXAMPLE 4

Preparation of Hair Growing Tonic 4

First, 70 g of ethyl alcohol, 10 g of 1,3-butyleneglycol, 0.5 g of N-acetylglutamine isostearyl ester, 0.25 of polyoxyethylene(25) glyceryl pyroglutamate isostearate diester, and 1 g of hexadecylphosphocholine (produced by Sigma Co.) were uniformly mixed and stirred to prepare a solution A.

Then, 18.25 g of pure water was added to the solution A with stirring, and uniformly mixed to prepare a hair-growing agent tonic (composition 4).

REFERENCE EXAMPLE 1

Determination of PKC-$IC_{50}$ and PKA-$IC_{50}$

According to the PKC-inhibiting activity measuring method and the PKA-inhibiting activity measuring method mentioned hereinabove, the PKC-inhibiting activity and the PKA-inhibiting activity of polymyxin B sulfate, calphostin C, and palmitoyl-DL-carnitine hydrochloride and hexadecylphosphocholine were measured, from which were obtained their PKC-$IC_{50}$ and PKA-$IC_{50}$.

The data obtained are shown in Table 1 below.

TABLE 1

| Tested Compound | PKC-$IC_{50}$ ($\mu$M) | PKA-$IC_{50}$ ($\mu$M) | PKA-$IC_{50}$/PKC-$IC_{50}$ |
|---|---|---|---|
| Polymyxin B Sulfate | 10 | >100 | >10 |
| Calphostin C | 0.05 | >50 | >1000 |
| Palmitoyl-DL-carnitine Hydrochloride | 100 | >300 | >3 |
| H-7[*1] | 15 | 13 | 0.87 |
| K252a[*1] | 0.02 | 0.02 | 1 |
| Staurosporine[*1] | 0.0027 | 0.0054 | 2 |

[*1]Excerpt from BIO/TECHNOLOGY, 8, 732, 1990.

REFERENCE EXAMPLE 2

Preparation of Tonic 5 to 9 Containing Staurosporine

To the mixed solution containing 90 g of ethyl alcohol, 5 g of 1,3-butyleneglycol, 0.5 g of N-acetylglutamine isostearyl ester and 0.25 g of polyoxyethylene(25) glyceryl pyroglutamate isostearate diester added $1\times10^{-6}$ g, $3\times10^{-6}$ g, $1\times10^{-5}$ g or $3\times10^{-5}$ g, $1\times10^{-4}$ g of Staurosporine, and was uniformly mixed and stirred to prepare 5 kinds of solution.

To these solutions was added 4.22 g of pure water respectively with stirring, and uniformly mixed to prepare hair growing tonics containing 0.02 $\mu$M (composition 5), 0.06 $\mu$M (composition 6), 0.2 $\mu$M (composition 7), 0.6 $\mu$M (composition 8), 2 $\mu$M (composition 9) or Staurosporine.

TEXT EXAMPLE 1

Hair Growth Promoting Effect in Mouse Hair-Follicle Cell Culture

Mouse hair-follicle-cells were cultivated and collected, according to the modified method of the Tanigai et al's method (Archives of Dermatological Research, 284, 290–296, 1992) while suitably modifying the method.

That is, the skin was peeled from the back of a 4-day age C3H mouse (bought from Nippon Charles River Co.), and processed with an MEM (Minimum Essential Medium, Eagle) containing 500 units/ml Disperse (produced by Godo Shusei Co.) and 5% FCS, at 4° C. for 16 hours.

The epidermis was removed from said skin sample, and the resulting dermis layer was processed with a DMEM (Dulbecco's Modified Eagle Medium) containing 0.25% collagenase N-2 (produced by Nitta Gelatin Co.) and 10% FCS, at 37° C. for 1 hours, to prepare a dermis suspension.

This dermis suspension was filtrated through a 212-micron nylon mesh (produced by Nippon Rikagaku Kikai K K), and the resulting filtrate was centrifuged at 1,000 rpm for 5 minutes to obtain hair-follicle tissue-containing pellets.

The resulting pellets were suspended in a Ca-Mg-free PBS (Dulbecco's Phosphate-Buffered Saline), using a pipette, and then statically left as it was for 15 minutes, whereby the hair-follicle tissue was precipitated.

The thus-obtained hair-follicle tissue was repeatedly processed for a total of three times according to the same process as above comprising the addition of a Ca-Mg-free PBS, the suspension with a pipette, and the precipitation for 15 minutes.

The hair-follicle tissue thus obtained finally was processed with 0.1% EDTA-0.25% trypsin (produced by Gibco Co.) at 37° C. for 5 minutes, to which was then added a DMEM containing 10% FCS. Thus was prepared herein a hair-follicle tissue cell suspension comprising $3\times10^5$ cells/ml.

This hair-follicle tissue cell suspension was pipetted into a 24-well collagen-coated plate (produced by Iwaki Glass Co.) in an amount of 1 ml/well, and cultivated at 37° C. in 5% $CO_2$ for 24 hours.

The resulting culture was then subjected to medium exchange with an MCDB153 medium (produced by Kyokuto Pharmaceutical Co.) containing 5 mg/liter insulin from bovine (produced by Sigma Co.), 5 $\mu$g/liter mouse EGF (produced by Takara Shuzo Co.), 40 mg/liter bovine pituitary extract (produced by Kyokuto Pharmaceutical Co.), 10 mg/liter human transferrin (produced by Sigma Co.), 0.4 mg/liter hydrocortisone (produced by Sigma Co.), 0.63 $\mu$g/liter progesterone (produced by Collaborative Research Co.), 14 mg/liter O-phosphoethanolamine (produced by Sigma Co.), 6.1 mg/liter ethanolamine (produced by Sigma Co.), 50 U/ml penicillin (produced by Wako Co.), 50 $\mu$g/ml streptomycin (produced by Wako Co.), and an DMSO solution comprising a PKC inhibitor of the invention (this was added in an amount of 1/100 by volume relative to the medium), and then further cultivated at 37° C. in 5% $CO_2$ for 5 days. During the incubation, the medium was exchanged with a fresh one every other day.

As the control, the cell culture was cultivated in the same manner as above, except that only DMSO of 1/100 by volume relative to the medium was added to the medium in place of the PKC inhibitor-containing DMSO solution.

To determine the degree of cell growth, referred to herein was a known method of using Neutral Red (see Journal of Tissue Culture Method, 9, 1, 7–9, 1984).

The resulting culture was extracted through suction, and then further cultivated in an MCDB153 medium, to which had been added 50 mg/liter Neutral Red (produced by Sigma Co.), at 37° C. in 5% $CO_2$ for 3 hours. The supernatant was removed from the culture, and the remaining cells were washed with a 1% formalin solution containing 1% calcium chloride, and then fixed.

After having been thus washed and fixed, the supernatant was removed, and a 50% ethanol solution containing 1% acetic acid was added to the residue in an amount of 0.4 ml/well of 2 $cm^2$, whereby Neutral Red was extracted out.

The absorbance of the extract at 540 nm was measured, from which was obtained the degree of growth of the cells.

The cell growth-promoting activity of each tested compound of the invention tested herein is shown in Table 2 below. As in Table 2, the hair-growing agent comprising each compound of the invention exhibits an excellent hair-growing effect of the mouse hair-follicle cell.

On the other hand, protein kinase inhibitors, K252a and Staurosporine, having $PKA-IC_{50}/PKC-IC_{50}$ of smaller than 3 were tested in the same manner as above, and the data obtained are shown in Table 3 below. As in Table 3, these protein kinase inhibitors inhibited the growth of mouse hair-follicle cells.

TABLE 2

| Compound Tested | Concentration ($\mu$M) | Relative Degree of Cell Growth, vehicled on the degree of cell growth of 100 in Control |
|---|---|---|
| Polymyxin B Sulfate | 10 | 360 |
| Calphostin C | 0.1 | 160 |
| Palmitoyl-DL-carnitine Hydrochloride | 10 | 170 |

TABLE 3

| Compound Tested | Concentration ($\mu$M) | Relative Degree of Cell Growth, vehicled on the degree of cell growth of 100 in Control |
|---|---|---|
| K252a | 0.00001 | 80 |
|  | 0.0001 | 77 |
|  | 0.001 | 76 |
|  | 0.01 | 29 |
|  | 0.1 | 0 |
| Staurosporine | 0.00001 | 78 |
|  | 0.0001 | 69 |
|  | 0.001 | 72 |
|  | 0.01 | 34 |
|  | 0.1 | 0 |

TEST EXAMPLE 2

Effect on Mouse Hair Growth

The compositions prepared hereinabove were tested for their effects on the growth of hair of mice, with reference to the Ogawa et al's method (see The Journal of Dermatology, Vol. 10, pp. 45–54, 1983).

Precisely, 9-week age, male C3H/HeSlc mice, of which the hair cycle was in the resting period, were grouped into plural groups each comprised of 4 or 5 mice. The hair on the back of each mouse was carefully shaven, using electric hair clippers and an electric shaver, and any of the compositions 1 to 4 as prepared in Examples 1 to 4 and Reference Example 2 was uniformly applied to the shaven part of each mouse, once a day in an amount of 200 $\mu$l/part.

To the mice of the control group, applied was the same composition as above except that it did not contain the protein kinase inhibitor of the invention.

On the 18th day after the start of the application of the composition to mice, the shaven skin on the back of each mouse was peeled and photographed. The photographic pictures obtained were imaged, using an image processor (produced by Avionics Co., Spicca II), whereby the percentage of the hair-grown area relative to the total area of the shaven skin was obtained to be the degree of hair growth. The value, by which the value of hair-growing percentage of the group to which the chemical had been applied is subtracted from the value of hair-growing percentage of the control group, was obtained to be the percentage of area with increased hair growth (%).

The data obtained herein a-re shown in Table 4 and Table 5 below.

As shown in Table 4, the hair-growing agents comprising the protein kinase C-specific inhibitor of the invention (composition 1 to 4) exhibit an excellent hair-growing effect of the mouse hair-follicle.

On the other hand, as shown in Table 5, no or little such effect was exhibited by using composition 5 to 9 containing Staurosporine which is protein kinase inhibitor having PKA-IC50/PKC-IC50 of smaller than 3 (composition 5 to 9).

TABLE 4

| Test Composition | Percentage of Area with Increased Hair Growth (%) |
|---|---|
| Composition 1 | 58 |
| Composition 2 | 65 |
| Composition 3 | 51 |

TABLE 5

| Test Composition | Concentration of Staurosporine ($\mu$M) | Percentage of Area with Increased Hair Growth (%) |
|---|---|---|
| Composition 5 | 0.02 | −2 |
| Composition 6 | 0.06 | −5 |
| Composition 7 | 0.20 | 3 |
| Composition 8 | 0.60 | −8 |
| Composition 9 | 2.00 | −14 | as has been mentioned in detail hereinabove, the present invention provides a safe and effective hair-growing agent comprising a protein kinase C-specific inhibitor.

While the invention has been described in detail and with reference to specific embodiments thereof, it will be apparent to one skilled in the art that various changes and modifications can be made therein without departing from the spirit and scope thereof.

What is claimed is:

1. A composition for percutaneous administration which promotes growth of hair-follicles, comprising, as an active ingredient, at least one selected from the group consisting of protein kinase C-specific inhibitors and pharmaceutically acceptable salts thereof, in a vehicle, wherein the protein kinase C-specific inhibitor is a protein kinase inhibitor in which a ratio of its 50% protein kinase A-inhibiting constant to its 50% protein kinase C-inhibiting constant is not smaller than 3.0, the active ingredient being included in an amount effective to promote growth of hair follicles, wherein the protein kinase C-specific inhibitor is selected from the group consisting of calphostin C, palmitoyl-DL-carnitine and hexadecylphosphocholine, wherein said vehicle is a carrier for a hair-follicle growing preparation, said carrier containing ethanol, and wherein the composition contains 55–90% ethanol.

2. The composition according to claim 1, wherein the protein kinase C-specific inhibitor is a protein kinase inhibitor in which a ratio of its 50% protein kinase A-inhibiting constant to its 50% protein kinase C-inhibiting constant is from 3.0 to $10^9$.

3. The composition according to claim 1, wherein the protein kinase C-specific inhibitor is a protein kinase inhibitor in which a ratio of its 50% protein kinase A-inhibiting constant to its 50% protein kinase C-inhibiting constant is from 10 to $10^9$.

4. The composition according to claim 1, wherein the amount of the protein kinase C-specific inhibitor contained in the composition is $10^{-6}$ to 10% by weight based on the composition.

5. A process for promoting hair follicle growth, comprising the step of:

applying percutaneously to hair follicles a protein kinase C-specific inhibitor or a pharmaceutically acceptable salt thereof, in an amount effective to promote hair follicle growth, wherein the protein kinase C-specific inhibitor is a protein kinase inhibitor in which a ratio of its 50% protein kinase A-inhibiting constant to its 50% protein kinase C-inhibiting constant is not smaller than 3.0, and wherein the protein kinase C-specific inhibitor is selected from the group consisting of calphostin C, palmitoyl-DL-carnitine and hexadecylphosphocholine.

6. The process according to claim 5, wherein the protein-kinase C-specific inhibitor is a protein kinase inhibitor in which a ratio of its 50% protein kinase A-inhibiting constant to its 50% protein kinase C-inhibiting constant is from 3.0 to $10^9$.

7. The process according to claim 5, wherein the protein kinase C-specific inhibitor is a protein kinase inhibitor in which a ratio of its 50% protein kinase A-inhibiting constant to its 50% protein kinase C-inhibiting constant is from 10 to $10^9$.

8. The composition according to claim 1, wherein the composition for percutaneous administration is selected from the group consisting of hair liquids, hair tonics, hair lotions, ointments and hair creams.

* * * * *